United States Patent [19]

Connolly et al.

[11] Patent Number: 4,513,096
[45] Date of Patent: Apr. 23, 1985

[54] SYNTHESIS GAS REACTION IRON CONTAINING ACTIVE CARBON CATALYSTS

[75] Inventors: John F. Connolly, Glen Ellyn; Arnold N. Wennerberg, Chicago; Robert F. Waters, Calumet City, all of Ill.

[73] Assignee: Standard Oil Company (Indiana), Chicago, Ill.

[21] Appl. No.: 643,158

[22] Filed: Aug. 22, 1984

Related U.S. Application Data

[62] Division of Ser. No. 497,401, May 23, 1983, Pat. No. 4,478,954.

[51] Int. Cl.$^3$ .................. B01J 23/86; B01J 23/85; B01J 23/76
[52] U.S. Cl. ........................ 502/185; 502/184
[58] Field of Search ................. 502/185, 184

[56] References Cited

U.S. PATENT DOCUMENTS

| | | | |
|---|---|---|---|
| 3,989,734 | 11/1976 | Alpert et al. | 518/715 |
| 4,423,156 | 12/1983 | Bussemeier | 518/715 |
| 4,447,665 | 5/1984 | Wennerberg | 502/185 |
| 4,478,954 | 10/1984 | Connolly et al. | 518/700 |

FOREIGN PATENT DOCUMENTS

5847 of 1915 United Kingdom ............... 502/185

OTHER PUBLICATIONS

Farley et al., J. Inst. of Petroleum, 50, No. 482, (1964) pp. 27–46.

*Primary Examiner*—P. E. Konopka
*Attorney, Agent, or Firm*—James R. Henes; William T. McClain; William H. Magidson

[57] ABSTRACT

A method of reacting carbon monoxide and hydrogen to form light hydrocarbons and alcohols in a slurry phase and in the presence of iron-containing active carbon catalyst is disclosed.

1 Claim, 1 Drawing Figure

SYNTHESIS GAS REACTION IRON CONTAINING ACTIVE CARBON CATALYSTS This is a division of application Ser. No. 497,401, filed May 23, 1983 now U.S. Pat. No. 4,478,954.

BACKGROUND OF THE INVENTION

1. Field of the Invention

This invention relates generally to the catalytic reaction between carbon monoxide and hydrogen to form hydrocarbons and more particularly concerns improvements in such reaction based upon the use of an improved iron-containing active carbon catalyst in a slurry phase.

2. Description of the Prior Art

Iron-containing catalysts are often employed in the synthetic production of hydrocarbons from gas mixtures containing carbon monoxide and hydrogen. It is highly desirable in such reactions to maximize the yield of unsaturated and oxygenated products from which chemicals and motor fuels with high octane ratings may be recovered.

A promising class of catalysts for use in the synthesis of hydrocarbons from carbon monoxide and hydrogen are active carbon compositions containing a metal component incorporated therein. It is known that the presence of metals in active carbon can greatly enhance the efficiency and selectivity of the active carbon when it is employed in catalytic, sorption, or filtering applications.

However, attempts to incorporate metal compounds into activated carbon by conventional physical impregnation techniques have been problematical. One disadvantage with physical impregnation of activated carbon with metal compounds is that the small pores at the surface of the active carbon particles are inaccessible to liquid penetration and prevent penetration of the liquid, metal-containing impregnating solutions, thereby rendering impossible uniform and thorough impregnation of the carbon particles with metal. Furthermore, physical impregnation of the active carbon causes partial blocking of the pores of the carbon particles resulting in an appreciable reduction of the active surface area thereof. In addition, it is not possible to control to any large extent the total quantity of the metal applied to the active carbon particles by impregnation and its distribution on and in the carbon particles, with the end result that there is a substantial risk that the metal will crystallize and agglomerate in an undesirable manner on the carbon particles.

Several techniques have been proposed to overcome the problems associated with impregnating active carbon with metal compounds. For example, Dimitry, U.S. Pat. No. 3,886,093 discloses activated carbons having uniformly distributed active metal sites and a method for making such activated carbons. The method of Dimitry involves mixing an aqueous solution of a lignin salt with an aqueous solution of a transition metal salt to precipitate the transition metal and lignin as a metal lignate. The transition metal must be capable of forming a chemical bond with the lignin and in so doing precipitating the lignin from solution as a metal lignate. Dimitry discloses that the time required to complete the precipitation is less than one hour and that usually 30 minutes is sufficient for this purpose. According to Dimitry, suitably the wet metal lignate precipitate can then be dried in a spray drier. Dimitry states that, although drying the metal lignate precipitate is not critical to form an activated carbon product, drying is necessary to form a high surface area end product. However, Dimitry gives neither a general disclosure nor a specific example of what it means by a "high surface" area for its end product. Dimitry states that the active metal sites are uniformly distributed throughout the activated carbon end product and presents an electron micrograph of an activated carbon end product magnified 5,700 times. However, from this relatively low magnification micrograph, the distribution of the active metal sites in the activated carbon end product is not readily apparent.

Furthermore, Siren, U.S. Pat. No. 4,242,226 states that the metal content in the active carbon which can be achieved by pyrolysis and activation of a metal lignate precipitate is much too low for the majority of fields of use and that it is difficult using such technique to predetermine the properties of the resulting metal-containing active carbon end product owing to the substantially undefined structure of the lignin. Siren discloses an alternative technique in which a cation of calcium, magnesium, barium, aluminum, copper or a transition metal and an anionic group chemically bound to a polyhexose derivative are caused to react in solution, and the resulting product is precipitated either spontaneously or by adding a suitable precipitating agent. Siren discloses that, after separating the precipitate from solution, the precipitate can, if desired, be dried, for example, by spray drying. Thereafter the separated reaction product is pyrolyzed and activated to form the activated carbon. In the method of Siren, suitably the polyhexose derivative employed comprises an acid polyhexose derivative and preferably the anionic groups of the polyhexose derivative comprise carboxylic acid groups, sulfonic acid groups or phosphoric acid groups. Preferably the polyhexose derivatives contain from 1 to 3 metal cations per hexose unit.

Wennerberg et al., U.S. Pat. No. 4,082,694 disclose a process for making a high surface area active carbon by first heating an agitated combination of solid potassium hydroxide containing between 2 and 25 weight percent water and a carbonaceous material comprising coal coke, petroleum coke or a mixture thereof below about 483° C., then heating the resulting dehydrated product at a temperature between 705° C. and 983° C. to thereby form active carbon, and finally cooling the resulting activated product and removing essentially all of the inorganic material therefrom by water washing to form the high surface area active carbon end product. The resulting product is a high surface area active carbon material which has a cage-like structure exhibiting a microporosity which contributes to over 60 percent of its surface and which has an effective BET surface area of greater than about 2500 square meters per gram and a bulk density greater than about 0.25 gram per cubic centimeter. Wennerberg et al., U.S. Pat. Nos. 3,642,657 and 3,817,874 and Wennerberg, U.S. Pat. No. 3,726,808 disclose related methods for making high surface area active carbon products.

More recently, in his copending patent application Ser. No. 470,285 and copending patent application Ser. No. 470,487, both filed on Feb. 28, 1983, and both of which in their entirety are specifically incorporated herein by reference, Wennerberg discloses an active carbon composition comprising a substantially uniform dispersion of a metal or metal-containing material in a porous carbon matrix, wherein the weight ratio of the metal or metal-containing material to active carbon matrix is from about 1:10000 to about 1:1, based on the weight of the metal or metal-containing material, respectively, and having a cage-like structure and a BET surface area of at least 800 square meters per gram and a bulk density of at least 0.1 gram per cubic centimeter, and two suitable methods for preparing such metal-containing active carbon compositions.

The preparation disclosed in Wennerberg's copending patent application Ser. No. 470,285 comprises the following steps: forming a uniform co-crystallite of a precursor of the metal or metal-containing material and of a carbon precursor, wherein the metal in the precursor of the metal or of the metal-containing material is a transition metal or a metal from Groups IIIA, IVA or VA of the Periodic Table of the Elements; forming a uniform powdered mixture of the co-crystallite and organic solids comprising an alkali metal hydroxide; pyrolizing the powdered mixture in an inert atmosphere at a temperature in the range of from about 400° C. to about 980° C. to form the carbon matrix having the metal or metalcontaining material substantially uniformly dispersed therein; and separating unreacted inorganic material and inorganic reaction products other than the dispersed metal or metal-containing material from the porous carbon matrix.

The method disclosed in Wennerberg's copending application Ser. No. 470,487 comprises the following steps: forming a carbon precursor which contains the metal by the chemical reaction in solution of (1) a soluble carbon precursor having at least one anionic group chemically bound thereto and (2) a soluble cation of a transition metal or metal from Groups IIIA, IVA or VA of the Periodic Table or a soluble cationic complex of such metal cation; precipitating and drying the metal-containing carbon precursor; forming a uniform powdered mixture of the metal-containing carbon precursor and inorganic solids comprising an alkali metal hydroxide; pyrolyzing the powdered mixture in an inert atmosphere at a temperature in the range of from about 400° C. to about 980° C. to form the carbon matrix having the metal or metal-containing material substantially uniformly dispersed therein; and separating unreacted inorganic material and inorganic reaction products, other than the dispersed metal or metal-containing material, from the carbon matrix to form the high surface area, porous carbon matrix end product.

The synthesis of hydrocarbons from carbon monoxide and hydrogen in a liquid phase slurry containing a catalyst has been performed in the past. Although it permits very good control of the reaction temperatures, the use of a slurry of catalyst in a liquid phase for this reaction generally has necessitated an additional step for the separation of the product from the catalyst and the use of modest space velocities.

Thus far, no one has disclosed a metal-containing active carbon catalyst for use in a liquid phase system which affords improved yields of light olefins and alcohols from the reaction between carbon monoxide and hydrogen, which minimizes the need for an additional step for the separation of product from the catalyst and which permits the use of high space velocities.

OBJECTS OF THE INVENTION

It is therefore a general object of the present invention to provide an improved method and catalyst for the synthesis of hydrocarbons from carbon monoxide and hydrogen which meets the aforementioned requirements and solves the aforementioned problems.

More particularly it is an object of the present invention to provide an improved aforesaid method and catalyst which afford improved yields of light olefins and alcohols.

Another object of the present invention is to provide an improved aforesaid method and catalyst which permit the use of a liquid phase containing a slurry of the catalyst which minimizes the need for an additional step to separate the catalyst from the product and which permits the use of high space velocities.

An additional object of the present invention is to provide an improved aforesaid method and catalyst which minimize catalyst deactivation.

Other objects and advantages of the invention will become apparent upon reading the following detailed description and appended claims, and upon reference to the accompanying drawings.

SUMMARY OF THE INVENTION

These objects are achieved by an improved method for converting carbon monoxide and hydrogen to hydrocarbons of high light olefin and alcohol content, comprising: combining carbon monoxide and hydrogen in synthesis proportions and under synthesis conditions comprising temperatures in the range of from about 290° C. to about 350° C. in a slurry in a liquid that is substantially sulfur-free inert under the synthesis conditions, of an active carbon catalyst comprising a substantially uniform dispersion of at least one of a chromium component, an aluminum component, a manganese component or a tungsten component in a porous carbon matrix and elemental iron either deposited thereon or substantially uniformly dispersed therein, wherein the concentration of active carbon in the catalyst is from about 20 to about 90 weight percent, based on the weight of the catalyst, wherein the concentration of elemental iron in the catalyst is from about 5 to about 50 weight percent, based on the weight of the catalyst, and wherein the total concentration of the chromium component, the aluminum component, the manganese component and the tungsten component or a combination thereof is from about 5 to about 40 weight percent, based on the weight of the catalyst and calculated as the elemental metal or metals.

The present invention is also the catalyst employed in the aforesaid method.

BRIEF DESCRIPTION OF THE DRAWING

For a more complete understanding of this invention, reference should now be made to the embodiment illustrated in greater detail in the accompanying drawing and described below by way of examples of the invention. In the drawing.

Figure 1:
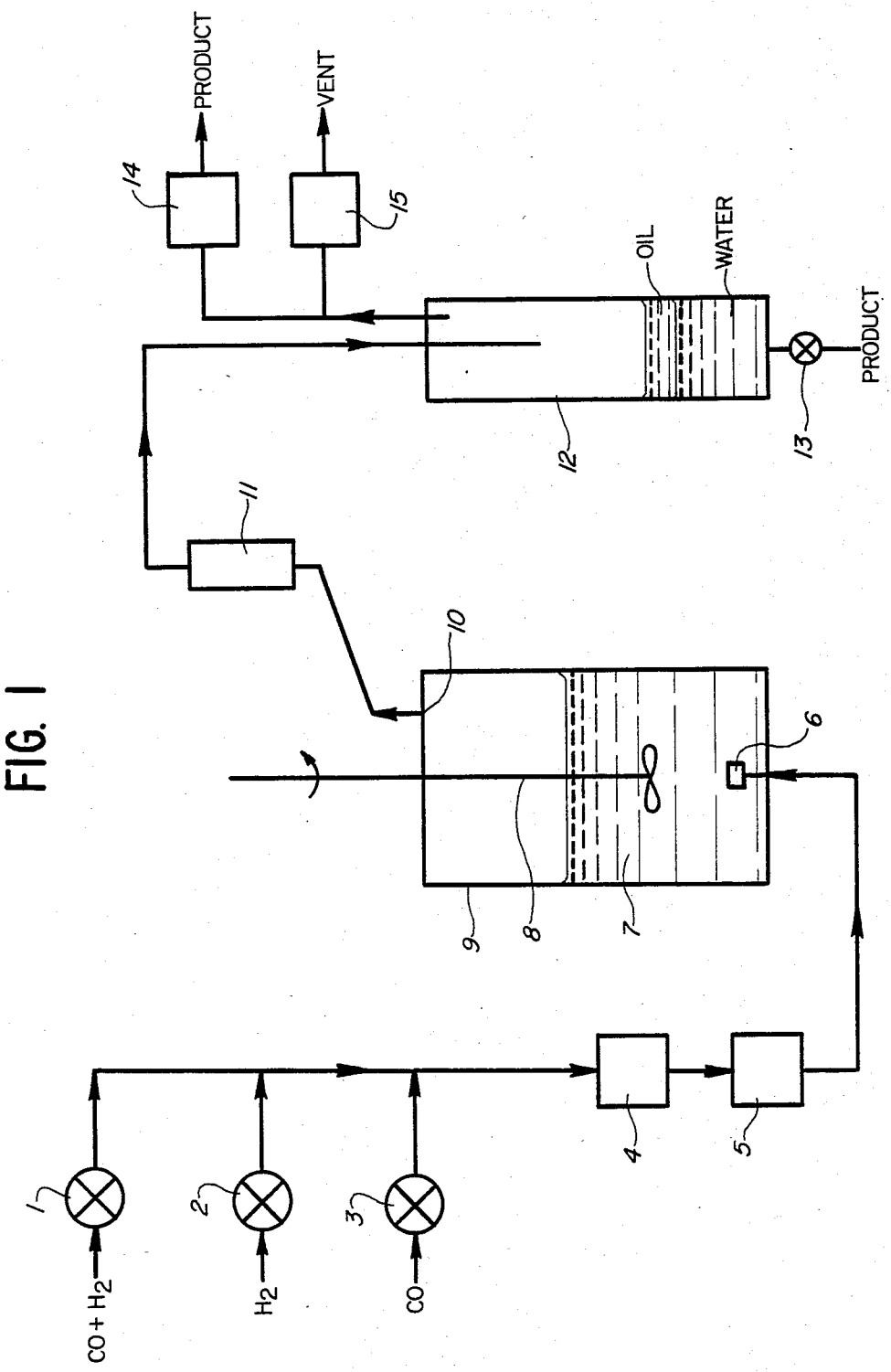
FIG. 1 is a schematic illustration of one embodiment of the method of this invention employing a stirred slurry of metal-containing active carbon catalyst in a slurry liquid.

It should be understood that the drawing is not to scale and is schematic in nature. In certain instances, details which are not necessary for an understanding of the present invention or which render other details difficult to perceive may be omitted. It should be understood, of course, that the invention is not necessarily limited to the particular embodiments illustrated herein.

DETAILED DESCRIPTION OF THE DRAWING INCLUDING PREFERRED EMBODIMENTS

The improved metal-containing catalyst employed in the method of this invention permits substantially improved yields of light olefins—primarily, ethylene and propylene—and of light alcohols—primarily, ethanol and propanol—from the reaction of carbon monoxide and hydrogen. The catalyst comprises active carbon at a level of from about 20 to about 90, preferably from about 30 to about 40, weight percent of the catalyst, based on the weight of the catalyst. The catalyst comprises elemental iron at a level of from about 5 to about 50, preferably from about 15 to about 40 weight percent, based on the weight of the catalyst. The catalyst also comprises a total concentration of the chromium component, the aluminum component, the manganese component or the tungsten component or a combination thereof at a level of from about 5 to about 40 weight percent, preferably from about 15 to about 35 weight percent, based on the weight of the catalyst and calculated as the elemental metal or metals. Each of the chromium component, aluminum component, manganese component and tungsten component can be in the form of its respective elemental metal or of a compound, for example, an oxide, of the respective metal. Optionally, the catalyst additionally comprises a promoter for the iron wherein the promoter comprises a potassium component, a cesium component, a rubidium component, a zinc component or a manganese component and is deposited on the active carbon matrix. If present, the promoter is at a level preferably from about 0.2 to about 5 more preferably from about 1 to about 3, weight percent of the catalyst based on the weight of the catalyst and calculated as the metal oxide. Although the promoter can be in the form of the elemental metal, its oxide or a combination thereof, typically the potassium, cesium, rubidium or zinc promoter is in the form of its oxide.

The selectivity of the aforesaid metal-containing active carbon catalyst for the production of light olefins and alcohols in the method of this invention, results from the fact that at least the chromium, aluminum, manganese and tungsten components, and optionally the elemental iron component, are substantially uniformly dispersed throughout the catalyst. In turn, in order to produce a catalyst having the aforesaid properties, it is critically important to employ one of the methods disclosed by Wennerberg in his copending patent application Ser. No. 470,285 and in his copending patent application Ser. No. 470,487.

As employed in the preparation of the catalyst used in the method of the present invention, the method of Wennerberg disclosed in copending patent application Ser. No. 470,285 involves forming a uniform co-crystallite of a carbon precursor and of at least one precursor of at least one of the chromium component, the aluminum component, the manganese component and the tungsten component and optionally of elemental iron.

Suitable carbon precursors for use in such method include aromatic carboxylic acids, phenols, aromatic amines and salts of any such materials. Preferably, metal salts of the aforesaid aromatic carboxylic acids and phenols are employed as the aforesaid carbon precursors.

The aforesaid aromatic acid may be any compound having an acid radical directly or indirectly attached to the benzene ring. The acid radical may be COOH, $PO_3H_2$, etc. Other functional groups may be present without deleterious effect. Aromatic carboxylic acids are preferred and may be simple monocarboxylic acids, such as benzoic acid, or polycarboxylic acids, such as terephthalic, isophthalic, trimesic, and trimellitic, or polynuclear carboxylic acids, such as naphthoic acid, or polynuclear polycarboxylic acids, such as sulfur-free coke acids. It is also contemplated that the aromatic carboxylic acids may be derived from any suitable carbonaceous material which is subsequently oxidized to form the carboxylic acid. The feed material may be treated, when necessary or desired, to remove contaminants or undesirable elements. For example, petroleum coke has a metal content, but oxidation of petroleum coke with nitric acid serves the dual function of forming coke acid and removing metals. While sulfurfree petroleum coke acid having any degree of oxidation is suitable in the aforesaid catalyst preparation, the preferred petroleum coke acid is one having an elemental oxygen content of between about 20 to 30 weight percent.

Suitable precursors of the chromium component, the aluminum component, the manganese component, the tungsten component and the elemental iron component for use in the formation of the co-crystallite in the catalyst preparation, generally include salts or complexes of chromium, aluminum, manganese, tungsten and iron ions and more specifically include, for example, alkali metal dichromate, aluminate, permanganate and tungstate salts, ferric salts and ferric phenolate complexes.

Any technique can be employed to form the co-crystallite which affords uniform co-crystallization —that is, simultaneous crystallization—of the carbon precursor and the aforesaid metal precursor(s) and the formation of a substantially uniform co-crystallite thereof. Homogeneity of the co-crystallite mixture is essential to the ultimate formation of a uniform dispersion of the metal components in high surface area active carbon. A strongly preferred technique to form the uniform co-crystallite of the carbon precursor and aforesaid metal precursor(s) involves the formation of a stable solution of such precursors in a suitable solvent and spray drying such solution to dryness. In such technique, solvent removal must be carried out rapidly enough to maximize rapid, simultaneous and homogeneous co-crystallization of the precursors from solution. Spray drying provides the desired rapid evaporation to ensure rapid, simultaneous and uniform co-crystallization and formation of a homogeneous co-crystallite of the precursors.

In a spray drying system which is suitable for use in carrying out the spray drying step, a solution of the carbon precursor and of the aforesaid metal precursor(s) of the metal or metal-containing material is introduced into a drying chamber through a nozzle. An inert gas such as nitrogen or argon is introduced through a nozzle assembly to assist in atomizing the solution entering the drying chamber. A second larger volume of preheated gas, such as air or inert gas depending upon requirements to prevent oxidation, is introduced into the drying chamber in a cocurrent or countercurrent manner. This preheated gas treatment provides the necessary high vapor capacity to effect rapid evaporation of the solvent from the atomized droplets. The resulting dry co-crystallite powder is entrained in the drying gas stream and separated from the gas stream in a sequence of appropriate cyclones. Effective solid gas separation may be accomplished by two appropriate cyclones in series. Water vapor laden gas is usually discharged in the atmosphere, and co-crystallite powder passes downward in and from the cyclones for collection.

In the spray drying technique, it is of course essential that stable solutions of the carbon precursor and metal precursor(s) be employed. Although it is preferred that a single solution containing dissolved carbon precursor and dissolved metal precursor(s) be employed, it is also suitable to employ separate solutions, for example, with one containing the dissolved carbon precursor and the other containing the dissolved metal precursor(s). When two such solutions are employed, the two solutions are mixed upstream of the aforementioned nozzle and aspirated together into the aforementioned drying chamber. Although any convenient solvent can be employed, water is the preferred solvent.

In the spray drying technique, forms of each of the carbon precursor and of the metal precursor(s) which are both soluble in the solvent used or each soluble in one or the other of the solvents used must be employed. Variables which can be controlled to effect the necessary solubility of the precursors in the same solvent or of each precursor in a different solvent include the pH of the solvents, the concentration of the precursors in the solvents, and the forms in which the precursors are introduced into the solvents—for example, the identity of the salt(s) or complex(es) of the metal precursor(s). Water soluble forms of the carbon precursor include potassium, sodium, rubidium and ammonium salts of aromatic carboxylic acids and phenols in an alkaline aqueous solution and aromatic amine hydrochlorides in an acidic aqueous solution. Water soluble forms of the metal precursors include, for example, alkali metal dichromate, aluminate, permanganate and tungstate salts, ferric nitrate, ferric ammonium citrate and ferric phenolate complexes.

In the alternative, as employed in the preparation of the catalyst used in the method of this invention, the method of Wennerberg disclosed in copending patent application Ser. No. 470,487 involves forming in solution a precipitate of a carbon precursor containing at least one precursor of at least one of the chromium component, the aluminum component, the manganese component, and the tungsten component and optionally of elemental iron. In such case, the metal-containing carbon precursor is formed by chemical reaction of at least one cation or cationic complex containing at least one precursor of at least one of the chromium component, the aluminum component, the manganese component, and the tungsten component and optionally of elemental iron with an anionic group on one of the aforementioned suitable carbon precursors, wherein carbon precursor and the metal cation(s) or cationic complex(es) containing the metal precursor(s) are soluble in the solvent employed for this reaction. Since water is the preferred solvent, water-soluble metal cations or water-soluble cationic complexes of the metal precursor(s) and water soluble carbon precursors are preferred for use in the preparation of the catalyst employed in the method of this invention. It is of course a critical requirement of such technique that the metal cation or the cationic complex of the metal ion react with the carbon precursor in solution so as to form a chemical bond with at least one anionic group on the carbon precursor.

In such technique, the carbon precursor and metal cation(s) or cationic complex(es) of the metal precursor(s) are combined in the solvent employed and in the proportions necessary to achieve the desired concentration of metal or metal-containing material in the final product. Chemical reaction between the carbon precursor and the metal cation(s) or cationic complex(es) of the metal precursor(s) either occurs spontaneously or is induced by adjustment of any convenient solution parameter, for example, the temperature or pH. Depending upon the particular carbon precursor used and the particular metal cation(s) or cationic complex(es) of the metal precursor(s) used, the reaction product thereof either precipitates out spontaneously or is precipitated by addition of a suitable precipitating agent or by adjustment of the temperature or pH of the solution, or is dried to the desired dry substance content. The resulting precipitated reaction product is then separated from solution by filtration, centrifugation or the like and, if desired, washed to remove any excess metal salt solution. The separated precipitate is then dried.

The co-crystallite powder or the dried precipitate formed as described above is then intimately mixed with the inorganic solids comprising an alkali metal hydroxide. Preferably at least 25 weight percent of the inorganic solids is the alkali metal hydroxide. Although not intending to limit the scope of the present invention by any theoretical explanation, the role of the alkali metal hydroxide in the formation of the metal-containing active carbon is believed to occur by reaction with the carbon precursor during pyrolysis to thereby propagate the formation of active carbon. The particle size of the inorganic solids need only be sufficiently small to ensure that the inorganic solids disperse well enough in the aforesaid co-crystallite powder or dried precipitate that an intimate mixture is formed. The weight ratio of alkali metal hydroxide-to-co-crystallite or -to-dried precipitate in the resulting mixture is from about 1:1 to about 5:1, preferably from about 2:1 to about 4:1 and more preferably from about 2.5:1 to about 3.5:1.

Although a hydroxide of any metal of Group IA of the Periodic Table can be mixed with the co-crystallite or dried precipitate, potassium hydroxide is strongly preferred. In addition to its ready availability and relative low cost, potassium hydroxide is advantageous because it is highly soluble in water and its carboxylate salts are highly soluble in water. The use of potassium hydroxide also affords an active carbon end product having a substantially higher surface area than if another alkali metal hydroxide is employed.

Preferably the alkali-metal hydroxide is hydrated. The water of hydration serves to assist in lowering the fusion temperature of the alkali metal hydroxide and in producing a uniform melt of the co-crystallite or dried precipitate and the alkali metal hydroxide in the pyrolysis step before pyrolysis occurs, to thereby facilitate mixing of the alkali metal hydroxide and co-crystallite or dried precipitate before reaction occurs. Preferably the alkali metal hydroxide contains from 2 to 25 weight percent of water of hydration.

The inorganic solids can comprise, in addition to the alkali metal hydroxide, an alkali metal salt such as an alkali metal halide, carbonate, sulfate, phosphate, nitrate or oxide. Preferably potassium is the alkali metal in the alkali metal halide, carbonate, sulfate, phosphate, nitrate or oxide. In one variation, some or all of the alkali metal salt is mixed with the carbon precursor and metal precursor(s) prior to or during formation of the co-crystallite, for example, in the spray drying step.

The intimate mixture of either co-crystallite powder or dried precipitate and inorganic solids is then pyrolyzed under an inert atmosphere such as nitrogen gas.

The pyrolysis temperature is selected to be high enough to decompose the carbon precursor and less than the graphitization temperature of carbon, that is, from about 400° C. to about 980° C., preferably from about 700° C. to about 900° C. The rate of temperature increase to which the mixture of either co-crystallite or dried precipitate and inorganic solids is subjected in the pyrolysis chamber is preferably at least 35° C. per minute and more preferably at least 300° C. per minute. Such rates of temperature increases of at least several hundred degrees centigrade per minute are readily attainable with microwave heating. The use of higher rates at which the temperature of the mixture is raised from ambient temperature to the final pyrolysis temperature effectively neutralizes the tendency toward the formation of separate phases as a result of differences in the temperatures and rates at which the carbon precursor and metal precursor(s) pyrolyze. Such phase separation is manifested by relatively larger crystal growth for the metal component(s) dispersed in the active carbon and thus is detectable by a relative increase in the crystallite size and by relative decreases in the uniformity of dispersion of the metal component(s) and of the accessible surface area of the dispersed metal component(s).

In the pyrolysis step, the precursor of the chromium component, the aluminum component, the manganese component or the tungsten component, is converted to the chromium component, the aluminum component, the manganese component or the tungsten component, respectively; in addition, if a precursor of elemental iron is present, it is converted to an iron-containing material, for example, an iron oxide, in the pyrolysis step.

Following the pyrolysis step, while still under a blanket of inert gas, the pyrolysis chamber and its contents are cooled and the powdered pyrolysis product is suspended in a suitable liquid, preferably water, in the blanketed pyrolysis chamber and then transferred as a slurry to a receiver. The solvency of the slurry liquid must be controlled to ensure that the dispersed metal component(s) does not dissolve in the slurry liquid. For example, when substantially neutral water is employed as the slurry liquid, the resulting slurry of the powdered pyrolysis product is alkaline and has a pH of about 12. Under these conditions, if the chromium or aluminum component dispersed in the active carbon were in the form of amphoteric chromia or alumina, it would dissolve in the water and would thereby be removed from the active carbon. Since it is necessary to prevent solubilization of the dispersed metal component(s) in such cases, the pH of the water would have to be reduced to about 7.0–8.0 with a suitable acid solution such as acetic acid, or vapor such as carbon dioxide or acetic acid vapor, before being used to rinse and slurry the powdered pyrolysis product.

The slurry is then filtered to separate the powdered pyrolysis product from the slurry liquid. Thereafter the powdered product is purified by repeated washings with a suitable solvent, preferably water, to remove the alkali metal therefrom and yet to leave undissolved the dispersed metal component(s) in solid form in the active carbon matrix. When water is used as the wash solvent and when the dispersed metal component is chromia or alumina, the pH of the water should be from about 7.5 to about 8.5 to ensure dissolution of the alkali metal in the water but to prevent dissolution of the dispersed chromia or alumina. Since potassium salts are more soluble than the corresponding salts of the other alkali metals, it is highly preferred that potassium is the alkali metal in the alkali metal hydroxide, in the dried precipitate and in any alkali metal salt mixed with the co-crystallite prior to the pyrolysis step to facilitate removal thereof from the active carbon. Thereafter the powdered product is dried using any conventional and suitable drying technique.

As indicated hereinabove, it is only optional that a precursor of elemental iron be employed in the preparation of the co-crystallite or precipitate in solution leading to the formation of the active carbon. In the event that a precursor of elemental iron is not used in the preparation of the co-crystallite or precipitate in solution and the pyrolysis product does not contain an iron-containing material, then after the active carbon is produced using the above-described procedure and then dried, an iron salt is impregnated on the dry active carbon using any convenient conventional impregnation technique. As will be illustrated in the examples hereinbelow, it has been found that the benefits accruing from the substantial uniform distribution of the chromium component, aluminum component, manganese component and tungsten component in the active carbon catalyst employed in the method of this invention are not adversely affected if an iron salt is deposited on the active carbon after the active carbon is formed.

Since relatively large amounts of the iron salt are to be deposited on the active carbon matrix and since the solubility in water of many iron salts suitable for impregnation is relatively low, it is often necessary to perform the impregnation step and to dry the resulting iron salt-impregnated active carbon and then to repeat the impregnation and drying sequence until the active carbon has the desired iron content.

Thereafter, if desired, active carbon containing the iron-containing material uniformly dispersed therein or the iron salt deposited thereon can be impregnated with a salt of potassium, cesium, rubidium, zinc or manganese using any convenient conventional impregnation technique and then dried. The resulting active carbon composition is then ground and sieved to the desired range of particle sizes.

Since the iron component of the active catalyst employed in the method of this invention is elemental iron, the iron-containing material uniformly dispersed throughout the active carbon and the iron salt deposited on the active carbon must be reduced to elemental iron. The reduction can be effected by heating the iron-containing active carbon at a temperature of from about 300° C. to about 400° C. in the presence of hydrogen. The resulting active catalyst is stored under an inert atmosphere such as argon until it is transferred to the slurry in the reactor system for the practice of the method of this invention. In the alternative, reduction of the dispersed iron-containing material and of the deposited iron salt could be effected in the slurry reactor system of the method of this invention where the active carbon containing the iron-containing material dispersed therein or an iron salt depository therein is contacted with hydrogen (and carbon monoxide) at a temperature of from about 290° C. to about 350° C.

The metal-containing active carbon thus formed preferably has a bulk density which is preferably greater than about 0.3 gram per cubic centimeter.

Although the crystallite size of the substantially uniformly dispersed metal component(s) depends on the particular metal component(s) and the rate of increase of temperature to which the mixture of co-crystallite or precipitate powder and inorganic solid was subjected during the pyrolysis step of the method of this invention, the average crystallite size of the dispersed metal component(s) is generally in the range of from about 5Å to about 150Å.

The metal-containing active carbon catalysts employed in the method of the present invention possess substantially improved resistance to thermally or chemically induced sintering or recrystallization of the dispersed metal component(s) to form a dispersed metal component(s) of relatively larger crystallite size and relatively lower effective surface area. Upon exposure to high temperatures, for example, 900° C. to 1150° C. for 12 hours, or to certain chemical treatments, for example, with 106 percent phosphoric acid for 65 hours at 200° C., the crystals of dispersed metal component(s) recrystallize to form larger crystals.

The dried active carbon end product containing elemental iron and at least one of a chromium component, aluminum component, manganese component or tungsten component generally has a particle size of about 100 microns and in that size range is suitable for use in the slurry system employed in the practice of the method of this invention. However, it may be desirable in certain instances to further reduce the particle size of the metal-containing active carbon catalyst. In such cases, the active carbon catalyst can be milled by any convenient method to small particle sizes. A major advantage of the uniform distribution of metal component(s) is that reduction of the particle size by milling or attrition does not affect the distribution of the dispersed metal component(s) within the active carbon or on its exterior surface and hence of the availability or accessibility of the dispersed metal component component(s). In such case, it is preferred that not only the chromium, aluminum, manganese and tungsten components, but also the elemental iron be uniformly dispersed throughout the active carbon matrix.

The method of the present invention is performed at a temperature in the range of from about 290° C. to about 350° C. with a hydrogen partial pressure in the range of from about 3.5 to about 84 kilograms per square centimeter, with a ratio of from about 1:1 to about 6:1, preferably from about 1.8:1 to about 5:1, moles of hydrogen per mole of carbon monoxide, at a space velocity of from about 0.132 to about 3.74, preferably from about 0.374 to about 2.42, standard liters of carbon monoxide per hour per gram of catalyst and with a slurry concentration of from about 5 to about 50, preferably from about 10 to about 30, weight percent of catalyst in the slurry liquid, based on the weight of the slurry.

The slurry liquid employed in the method of this invention can suitably be any liquid which is substantially sulfur-free and inert under the synthesis conditions employed. A liquid that contains no more than 10 parts per million of sulfur is substantially sulfur-free for present purposes. A liquid that does not boil, react or interface with the performance of the catalyst is substantially inert in the present context. In addition, preferably the slurry liquid is organic and miscible with any heavy liquid products formed under the synthesis conditions which may remain in the slurry system. Typically the slurry liquid is a paraffin such as dodecane, hexadecane, eicosane or a mixture of paraffins such as a white oil.

The use of a slurry system in the method of this invention offers numerous advantages. For example, the reaction between carbon monoxide and hydrogen is highly exothermic and requires that the generated heat be carried away. In the slurry system of this invention, the heat capacity of the slurry liquid facilitates carrying away the heat of reaction. In fact, the use of a liquid slurry system in the method of the present invention permits relatively higher reaction temperatures to be employed than in a gas phase system and thus promotes the formation of lower molecular weight products at the higher reaction temperatures. A further benefit is that the yield of higher boiling product which must be separated from the catalyst is reduced to only a few percent of the overall products.

Furthermore, the slurry system permits the features of the catalyst of this invention to be fully exploited in the method of this invention. The catalyst of this invention has a relatively small particle size and a relatively low mechanical strength and can be pelletized only with difficulty. Thus, use of the catalyst of this invention in a packed or fluidized bed is often problematical. However, the slurry system readily permits the small particle-size catalysts of this invention to be employed. In turn, use of the small particle-size catalyst of this invention shortens the diffusion path of the reactants into the catalyst and thereby reduces diffusion resistance limitations. Catalyst attrition is also greatly reduced in the slurry system. Furthermore, equipment damage resulting from the circulation of solid particles in a gas-solid stream is minimized by the use of the slurry system. The use of the small particle-size catalysts of this invention also greatly facilitates maintenance of a uniform dispersion of the catalyst particles in the slurry liquid.

A slurry system of any convenient conventional design can be employed. Designs which have been particularly suitable include a stirred reactor system and a bubble column reactor. A stirred slurry reactor that was employed in Examples 16–30 is illustrated in FIG. 1 and described hereinbelow in the discussion of Examples 16–30.

The present invention will be more clearly understood from the following specific examples.

EXAMPLES 1–15

The following is the general procedure that was employed in Examples 1–15 to make the catalysts which were employed in Examples 16–30.

Precursor salts of the active carbon and of the metal component(s) to be dispersed throughout the active carbon were dissolved in an aqueous solution. In each case, terephthalic acid was employed as the precursor of the active carbon. $K_2Cr_2O_7$, $NaAlO_2$, $KMnO_4$ and $Na_2WO_4 \cdot 5H_2O$ were employed as the precursor salts of the metal component(s) depending upon which metal component(s) was to be uniformly dispersed throughout the active carbon matrix. One equivalent of KOH and two equivalents of $K_2CO_3$ were also dissolved in the aqueous solution per equivalent of terephthalic acid to form the water-soluble potassium salt of terephthalic acid. The resulting solution was spray dried in an electrically heated, indirect fired spray dryer supplied by Bowen Company in the manner described generally hereinabove using nitrogen as the aspirating, drying and entrainment gas. This procedure resulted in a substantially uniform co-crystallite of the carbon precursor and precursor of the metal component(s).

The resulting powdered co-crystallite was blended with three equivalents of 90 percent solid potassium hydroxide containing 10 percent water per equivalent of terephthalic acid in the co-crystallite, under a dry nitrogen blanket and using a Waring blender.

The resulting blend was then pyrolyzed under an inert nitrogen blanket in a carbon steel pyrolysis tube which was rotated in an electrically heated, tubular furnace. The following temperature program and sequence was typical. The pyrolysis tube and its contents were heated to 371° C. where the temperature was held constant for 10 minutes to allow the hydrated potassium hydroxide to melt, mix well with the other components of the blend and partially dehydrate. The temperature of the tube contents was then raised to 399° C. and held at that temperature for five minutes, at which point dehydration was complete. Thereafter heating was resumed to raise the temperature of the tube's contents to 538° C., at which point heating was stopped, the furnace was opened and nitrogen was blown on the tube for approximately five minutes. This procedure served to permit the tube walls to cool and solids in the tube to fall or break away from the tube walls. The furnace was then closed and heating was resumed to raise the temperature of the tube and its contents to 648° C., at which point heating was discontinued, the furnace was opened and nitrogen was blown onto the tube for about five minutes, to again permit the tube walls to cool and solids in the tube to fall or break away from the tube walls. The furnace was again closed and heating was resumed to raise the temperature of the tube and its contents to a pyrolysis temperature between 843° C. and 954° C. where the temperature was held constant for about 12 hours. Heating was then discontinued, and the furnace was opened slightly and nitrogen was blown on the tube until its bright red color faded. Thereafter the furnace was opened completely, and the tube was kept under a blanket of nitrogen until it had cooled to a temperature at which it could be handled.

At this point, while still under the continuous blanket of nitrogen, the pyrolysis product was suspended in water and transferred as a slurry from the pyrolysis tube. Separation and purification of the powdered pyrolysis product from the slurry was accomplished by filtration followed by repeated washing with water to extract and remove all soluble inorganic material other than the metal component(s) dispersed in the active carbon matrix. When the dispersed metal component was $Al_2O_3$ or $WO_3$, and when substantially neutral water is employed as the slurry liquid, the resulting slurry of the powdered pyrolysis product would be alkaline and have a pH of about 12. Under these conditions, the $Al_2O_3$ or $WO_3$ dispersed in the active carbon matrix is amphoteric and would dissolve in the water and would thereby be removed from the active carbon matrix. Consequently, in such instances, it was necessary to lower the pH of the slurry and wash water to 7.5–8.5 to ensure that the dispersed $Al_2O_3$ and $WO_3$ did not dissolve in the slurry and wash water. Thereafter, in all cases, the final, washed and filtered pyrolysis product was dried.

In two cases, the solution that was spray dried additionally contained ferric ammonium citrate, a precursor of iron, and consequently an iron component was already present and was uniformly dispersed in the dried, filtered pyrolysis product. However, in all other cases, the iron component was not present in the pyrolysis product but was subsequently deposited thereon by impregnation of the pyrolysis product with a nearly saturated aqueous solution of ferric nitrate, and the impregnated active carbon was then dried. Because of the limited solubility of such iron salts in water, repeated impregnation steps were necessary in order to build up the desired concentration of iron in the active carbon. Consequently, incorporation of the iron salt into the active carbon support was accomplished by repeating the sequence of (1) impregnation of the support to the point of incipient wetness and (2) drying, until the metal-containing active carbon contained the desired concentration of iron.

Thereafter, the dried active carbon either having an iron salt deposited thereon or having an iron-containing material uniformly dispersed therein was impregnated with a potassium component by contacting the active carbon with a concentrated aqueous solution of potassium carbonate and then drying.

The resulting product had an average particle size of about 75 microns and was charged to a Vycor reactor tube equipped with an internal helical flight to ensure effective tumbling and exposure during rotation. The tube and its contents were placed in the cavity of a tubular furnace, supported for free rotation therein and connected to a gas supply. While purging the tube with argon, the temperature of the tube and its contents was raised to 449° C. and held at that temperature for 20 minutes to convert any iron salt to iron oxide. Thereafter, while still under the argon blanket, the tube and its contents were cooled to 260° C., at which point the argon flowing through the tube was replaced with hydrogen, and the tube and its contents were heated to 371° C. Reduction of the iron salts with hydrogen was complete after 16–18 hours of hydrogen treatment at about 371° C. The tube and its contents were then cooled to 260° C., at which point the hydrogen flowing through the tube was replaced with argon, and the system was allowed to cool to room temperature. While still under an argon blanket, the catalyst was transferred to a receiver vessel.

The following modifications of the aforesaid general procedure were employed. Example 1 is a comparative example in which the chromium component was not uniformly dispersed throughout the active carbon during formation of the active carbon, but instead was deposited on the active carbon after it had been formed. In Example 1, the spray drying step was omitted. Instead a blend of potassium terephthalate, potassium carbonate and potassium hydroxide was made, with the proportions used being those employed for potassium terephthalate, potassium carbonate and potassium hydroxide, respectively, in the combination of the spray drying and pyrolysis steps in the aforesaid general procedure. This blend was pyrolyzed, washed and dried as in the general procedure. Thereafter the resulting active carbon was repeatedly contacted with an aqueous solution of ammonium dichromate and then heated slowly to 316° C., to thereby impregnate the active carbon with a chromium component. The chromia-containing active carbon was then impregnated with iron and potassium oxide as in the aforedescribed general procedure.

In Example 3, prior to impregnation with the iron component, the dried active carbon pyrolysis product was oxidized by air at 343° C. to 388° C. In each of Examples 4 and 5, an aqueous impregnating solution containing rubidium carbonate or cesium carbonate, respectively, was also employed and additional promoter in the active catalyst was rubidium oxide or cesium oxide, respectively. In Example 6, the aqueous impregnating solution of ferric nitrate also contained manganese nitrate, and the final catalyst contained 2 weight percent of elemental manganese as the promoter; impregnation with a potassium salt was omitted. The final catalyst contained potassium which probably was a residue of potassium carbonate or potassium hydroxide introduced in the spray drying and pyrolysis steps, respectively, and remaining after the wash step. In each of Examples 7 and 8, an aqueous solution of ferric ammonium citrate, not ferric nitrate, was employed as the iron impregnating solution.

In each of Examples 9 and 11, the spray drier feed solution contained both potassium dichromate and sodium aluminate, and thus both chromium and aluminum components were uniformly distributed throughout the pyrolysis products. The pyrolysis product was treated with glacial acetic acid at 110° C. to lower the pH and thereby prevent solubilization of the dispersed alumina. In both examples, the total iron content of the final catalyst had two sources: one being impregnation with ferric ammonium citrate and the other being pick-up from the walls of the pyrolysis tube. In Example 9, of the total amount of iron on the final catalyst, about 55 percent came from the pyrolysis tube itself and was impregnated on the pyrolysis product during the pyrolysis step. In Example 10, the spray drier feed solution contained sodium aluminate instead of potassium dichromate, and thus an aluminum component instead of a chromium component was uniformly distributed throughout the pyrolysis product. In addition, the treatment with hot acetic acid as in Example 9 was repeated. A greater amount of potassium was impregnated on the catalyst. In Example 11, of the total amount of iron on the final catalyst, almost 60 percent came from the pyrolysis tube itself and was impregnated on the pyrolysis product during the pyrolysis step. In Example 12, the spray drier feed solution contained sodium tungstate instead of potassium dichromate, and thus a tungsten component instead of a chromium component was uniformly distributed throughout the pyrolysis product. In the pyrolysis step, hydrogen was used instead of nitrogen until the temperature reached 593° C. at which point argon replaced the hydrogen. Following the pyrolysis step, the pyrolysis product was slurried with a mixture of ethanol and glacial acetic acid to lower the pH and thereby to avoid solubilizing tungstate in the slurry and wash steps. Water was also added to the ethanol-glacial acetic acid slurry solution. A ferric salt was deposited on the pyrolysis product by impregnation thereof with ferric ammonium citrate. In each of Examples 13 and 14, ferric ammonium citrate was additionally dissolved in the spray drier feed solution and thus an iron-containing material was additionally uniformly dispersed throughout the active carbon matrix formed in the pyrolysis step. Furthermore, there was no potassium carbonate in the spray drier feed solution. In Example 14, the pyrolysis product was oxidized by air at 343° C. to 360° C. prior to the impregnation steps. In Example 15, prior to the impregnation step, the dried pyrolysis product was oxidized by contact with a gas mixture containing 2-7 volume percent of oxygen prior to the impregnation steps.

Apart from their potassium carbonate and potassium hydroxide contents, the spray drier feed solutions had the following compositions: Examples 2-8 and 13-15—6.8 weight percent of terephthalic acid and 2.6 weight percent of potassium dichromate; Example 9—5.1 weight percent of terephthalic acid, 1 weight percent of potassium dichromate and 0.8 weight percent of sodium aluminate; Example 10—7 weight percent of potassium terephthalate instead of terephthalic acid and 1.5 weight percent of sodium aluminate; Example 11—6.1 weight percent of terephthalic acid, 1.6 weight percent of potassium dichromate and 0.6 weight percent of sodium aluminate; and Example 12—6.1 weight percent of terephthalic acid and 1.8 weight percent of sodium tungstate.

The chemical compositions, BET surface areas and bulk densities of the catalysts produced in Examples 1-15 are shown in Table 1. In Table 1, the concentrations of the chromium, aluminum and tungsten components are calculated as the respective metal oxides and the promoters are calculated as oxides.

EXAMPLES 16-30

The catalysts prepared in Examples 1-15 were employed in Examples 16-30 to catalyze reactions between carbon monoxide and hydrogen in a stirred-slurry-reactor system. A schematic of the stirred-slurry-reactor system employed in Examples 16-30 is illustrated in FIG. 1. A mixture of hydrogen and carbon monoxide containing 35.71 weight percent of

TABLE 1

| Catalyst Prepared in Example No. | Composition (Wt %) | | | | Surface Area ($m^2$/gm) | Bulk Density (gm/cc) |
|---|---|---|---|---|---|---|
| | Carbon | Chromia | Elemental Iron | Potassium Oxide | | |
| 1 | 21.9 | 48.1 | 28.5 | 1.5 | 120 | 0.97 |
| 2 | 29.4 | 30.4 | 38.0 | 2.2 | 120 | 0.64 |
| 3 | 32.6 | 47.6 | 17.5 | 2.3 | 380 | 0.50 |
| 4 | 28.6 | 34.8 | 34.5 | 1.9[a] | 160 | 0.65 |
| 5 | 27.5 | 35.0 | 34.7 | 1.6[b] | 130 | 0.69 |
| 6 | 25.3 | 36.9 | 32.8 | 1.4[c] | 120 | 0.62 |
| 7 | 41.5 | 25.8 | 32.7 | | 700 | 0.88 |
| 8 | 41.5 | 25.8 | 32.7 | | 700 | 0.88 |
| 9 | 32.6 | 14.8[d] | 40.5 | 1.4 | 690 | 0.90 |
| 10 | 45.4 | [e] | 33.2 | 3.7 | 730 | 0.71 |
| 11 | 34.9 | 17.0[f] | 43.0 | 1.4 | 500 | 1.01 |
| 12 | 69.7 | [g] | 18.9 | 1.4 | 1950 | 0.57 |
| 13 | 36.3 | 27.3 | 33.0 | 3.4 | 200 | — |
| 14 | 26.1 | 33.0 | 38.0 | 2.8 | 75 | 0.48 |
| 15 | 22.6 | 40.0 | 34.6 | 2.7 | 77 | 0.69 |

Footnotes
[a] Additionally contains 0.18 weight percent of a rubidium component as promoter, calculated as $Rb_2O$.
[b] Additionally contains 1.20 weight percent of a cesium component as promoter, calculated as $Cs_2O$.
[c] Additionally contains 2.56 weight percent of a manganese component as promoter, calculated as elemental manganese.
[d] Additionally contains 10.64 weight percent of an aluminum component, calculated as $Al_2O_3$.
[e] Contains 17.65 weight percent of an aluminum component, calculated as $Al_2O_3$.
[f] Additionally contains 3.72 weight percent of an aluminum component, calculated as $Al_2O_3$.
[g] Contains 12.22 weight percent of a tungsten component, calculated as $WO_3$.

carbon monoxide—that is, 1.80 moles of hydrogen per mole of carbon monoxide—was employed as the basic feed gas to the stirred-slurry-reactor system and was introduced by opening valve 1. Feed gas to the stirred-slurry-reactor system having different compositions was made by introducing a stream of pure hydrogen or carbon monoxide to the aforesaid basic feed gas by opening valve 2 or valve 3, respectively. The resulting feed gas of the desired composition was purified by passage first through charcoal 4 and then through silica 5 and was then introduced through a gas dispersion frit 6 into a slurry 7 stirred by a stirrer 8 in the reactor 9.

The slurry liquid in the slurry 8 at the start of a run was 150 grams of hexadecane whose sulfur content had been previously reduced to less than three parts per million by weight by pretreatment of the hexadecane in a silica gel column. Vaporized product and unconverted feed gas were withdrawn from the stirred-slurry-reactor through a vent 10 near the top thereof and passed to a knock-back condenser 11 maintained at a temperature of 121° C. to 149° C. As the run proceeded, a small amount of hexadecane slurry liquid or products therefrom passed out of the reactor system and through the aforesaid condenser. This lost hexadecane liquid was gradually replaced by heavy product from the reaction between hydrogen and carbon monoxide. This addition of heavy product to the slurry liquid generally resulted in a substantially constant liquid level in the stirred-slurry-reactor system. However, when necessary or desired, the liquid level in the system was maintained at a substantially constant level either by the addition of hexadecane or by adjustment of the temperature of the overhead condenser during the run.

Vaporized product and unconverted feed gas passing through the condenser were then directed to a gas-liquid separator 12 maintained at room temperature where higher boiling product condensed and separated into oil and water layers which were withdrawn from the separator at 24- or 48-hour intervals by opening the valve 13. Gaseous material passed continuously through the gas-liquid separator and was vented through a wet test meter 14, with a slide stream of gas passing through a gas chromatograph sampling system 15. In addition to the analysis of this gas stream, analyses were conducted of the oil and water fractions collected in the gas-liquid separator and of the heavy products remaining in the slurry liquid in the reactor at the end of a run. The stirred-slurry-reactor system was maintained at a temperature of 315° C. in Examples 16–29 and at temperatures between 315° C. and 327° C. in Example 30, and at a pressure of 32.6 kilograms per square centimeter in Examples 16–24 and 28–30 and of 18.6 kilograms per square centimeter in Examples 25–27. The other parameters employed and the results from Examples 16–30 are reported in Tables 2 and 3, respectively.

and oxygen mass balances shown in Table 4 were obtained from the results of the aforesaid analyses.

TABLE 2

| Example | Catalyst from Example | Catalyst Weight (Grams) | CO Space Velocity | Moles $H_2$ per Mole CO |
|---|---|---|---|---|
| 16 | 1 | 13.3 | 0.936 | 1.8 |
| 17 | 2 | 24.7 | 0.543 | 3.0 |
| 18 | 3 | 24.4 | 0.561 | 3.0 |
| 19 | 4 | 24.2 | 0.561 | 3.0 |
| 20 | 5 | 24.1 | 0.574 | 3.0 |
| 21 | 6 | 25.1 | 0.549 | 3.9 |
| 22 | 7 | 12.1 | 1.073 | 3.1 |
| 23 | 8 | 13.0 | 0.967 | 3.1 |
| 24 | 9 | 10.6 | 0.729 | 3.4 |
| 25 | 10 | 9.6 | 0.761 | 4.3 |
| 26 | 11 | 9.5 | 0.823 | 4.2 |
| 27 | 12 | 11.8 | 0.655 | 1.8 |
| 28 | 13 | 26.9 | 0.655 | 1.8 |
| 29 | 14 | 12.1 | 0.524 | 1.8 |
| 30 | 15 | 20.8 | 0.605 | 1.8 |

TABLE 3

| Example | Total CO Percent Conversion | Catalyst Activity | Selectivities Methane | Light Olefin |
|---|---|---|---|---|
| 16 | 86 | 110 | 17 | 13 |
| 17 | 96 | 300 | 11 | 25 |
| 18 | 92 | 170 | 12 | 24 |
| 19 | 95 | 300 | 11 | 23 |
| 20 | 96 | 300 | 11 | 24 |
| 21 | 97 | 600 | 15 | 24 |
| 22 | 37 | 40 | 12 | 27 |
| 23 | 94 | 270 | 14 | 32 |
| 24 | 83 | 70 | 12 | 35 |
| 25 | 67 | 40 | 10 | 28 |
| 26 | 86 | 100 | 12 | 33 |
| 27 | 91 | 130 | 12 | 27 |
| 28 | 83 | 60 | 8 | 26 |
| 29 | 92 | 140 | 11 | 25 |
| 30 | 92 | 120 | 11 | 30 |

TABLE 4

| Analysis After Day | Temperature | Total CO Percent Conversion | Carbon Balance | Oxygen Balance | Selectivities | | | | | |
|---|---|---|---|---|---|---|---|---|---|---|
| | | | | | $CH_4$ | $C_2H_4$ | $C_3H_6$ | $1-C_4H_8$ | $C_2-C_4$ Non-Olefins | $C_5+$ |
| 3 | 600 | 92.4 | 1.02 | 1.00 | 10.3 | 13.7 | 13.3 | 7.5 | 8.3 | 46.9 |
| 4.5 | 600 | 91.9 | 1.02 | 1.00 | 10.4 | 13.8 | 14.3 | 8.2 | 8.0 | 44.2 |
| 6 | 600 | 91.8 | 1.01 | 0.94 | 10.2 | 13.7 | 13.8 | 7.8 | 7.9 | 45.0 |
| 7 | 600 | 92.3 | 1.05 | 1.04 | 11.4 | 15.7 | 17.5 | 8.7 | 8.8 | 37.9 |
| 9 | 600 | 93.0 | 0.94 | 0.95 | 9.7 | 12.9 | 15.5 | 7.3 | 7.6 | 43.1 |
| 11.5 | 600 | 92.5 | 1.02 | 1.01 | 10.5 | 13.1 | 14.1 | 8.0 | 8.5 | 47.1 |
| 13 | 600 | 91.8 | 1.03 | 1.03 | 11.5 | 14.3 | 16.7 | 8.5 | 9.1 | 39.5 |
| 15 | 600 | 91.6 | 1.00 | 1.01 | 10.9 | 14.0 | 14.1 | 8.0 | 8.7 | 43.4 |
| 17 | 600 | 90.7 | 0.99 | 1.01 | 11.4 | 14.3 | 14.6 | 8.5 | 8.8 | 41.2 |
| 19 | 600 | 93.1 | 0.99 | 0.98 | 10.9 | 17.6 | 13.9 | 7.8 | 8.9 | 40.7 |
| 21 | 600 | 93.0 | 0.98 | 1.00 | 10.9 | 14.7 | 14.1 | 7.9 | 8.7 | 43.1 |
| 23 | 600 | 93.4 | 0.97 | 0.99 | 10.9 | 14.5 | 14.3 | 7.9 | 8.8 | 43.4 |
| 25 | 600 | 92.9 | 1.02 | 1.02 | 11.7 | 13.7 | 15.2 | 8.5 | 9.3 | 39.8 |
| 27 | 600 | 92.2 | 1.00 | 1.04 | 11.5 | 11.6 | 15.1 | 8.4 | 9.2 | 43.8 |
| 29 | 600 | 91.7 | 1.00 | 1.01 | 11.0 | 13.5 | 14.4 | 8.0 | 8.8 | 43.7 |
| 31 | 600 | 91.7 | 0.98 | 1.01 | 11.5 | 13.9 | 14.6 | 8.2 | 9.1 | 42.4 |
| 33 | 605 | 92.6 | 1.03 | 1.01 | 11.0 | 14.9 | 17.6 | 8.2 | 8.3 | 35.4 |
| 35 | 605 | 92.1 | 1.02 | 1.01 | 11.3 | 13.9 | 17.6 | 8.2 | 8.7 | 36.5 |
| 37 | 610 | 92.0 | 1.02 | 1.03 | 12.2 | 14.5 | 15.6 | 8.5 | 9.7 | 39.2 |
| 39 | 610 | 92.0 | 1.00 | 1.01 | 11.4 | 14.5 | 17.9 | 8.1 | 9.4 | 39.5 |
| 43 | 615 | 91.3 | | 1.01 | 11.8 | 14.1 | 14.7 | 8.0 | 9.6 | 41.6 |
| 45 | 620 | 91.6 | 1.02 | 1.00 | 11.7 | 14.0 | 17.8 | 8.2 | 8.9 | 35.9 |
| 49 | 620 | 90.9 | 1.03 | 1.01 | 11.8 | 14.2 | 17.8 | 8.2 | 9.1 | 35.0 |
| Average | | 92.1 | 1.01 | 1.01 | 11.1 | 14.1 | 15.4 | 8.1 | 8.8 | 41.2 |

Example 30 was a 50-day run for which more detailed results are presented in Table 4. The complete carbon In general, it is preferred to have low methane selectivities, high total carbon monoxide percent conversions and high light olefin, ethylene, propylene and 1-butene selectivities. Comparison of the results in Table 3 for Example 16 employing the comparison catalyst with the results for Examples 17-30 employing the catalyst of the present invention indicates lower methane selectivities and higher light olefin selectivities for the catalysts of the present invention relative to those for the comparison catalyst.

Furthermore, comparison of the values in Table 3 of the methane and light olefin selectivities for Examples 28 and 29 with those for Examples 17-27 and 30 indicates that such selectivities are not strongly dependent on whether or not the iron component of the catalyst is deposited thereon or substantially uniformly distributed therein.

In Table 2, the space velocity is expressed in units of standard liters of carbon monoxide per gram of catalyst per hour. In Tables 3 and 4, the total carbon monoxide percent conversion is product obtained by multiplying 100 by the quotient obtained by dividing the difference between the amount of carbon monoxide in the feed and product streams by the amount of carbon monoxide in the feed. The methane, light olefin, ethylene, propylene, 1-butene, $C_2$-$C_4$ non-olefins and $C_5+$ selectivities in Tables 3 and 4 are the percentages of the portion of carbon monoxide converted to products other than carbon dioxide which are converted to methane, ethylene, propylene, 1-butene, $C_2$-$C_4$ non-olefins and $C_5+$, respectively. Included in the values of light olefin selectivities in Table 3 are contributions from ethanol and propanol (both calculated from dehydration) produced as well as light olefins. Included in the values of ethylene, propylene and $C_2$-$C_4$ non-olefin selectivities in Table 4 are contributions from ethanol, propanol and 2-butene produced, respectively, as well as ethylene, propylene and $C_2$-$C_4$ non-olefins, respectively.

The results in Table 4 illustrate the stability and efficiency of the catalyst over the 49 day test period. A similar run extending 50 days but instead in a bubble column slurry reactor employing a much higher space velocity of 2.8 standard liters of carbon monoxide per hour per gram of catalyst yielded 1200 grams of product per gram of catalyst during the run and showed no evidence of deactivation.

While the invention is described in connection with the specific examples, it is to be understood that these are for illustrative purposes only. Many alternatives, modifications and variations will be apparent to those skilled in the art in the light of the below examples and such alternatives, modifications and variations fall within the scope and spirit of the appended claims.

What is claimed is:

1. An active carbon catalyst comprising a substantially uniform dispersion of at least one of a chromium component, an aluminum component, a manganese component or a tungsten component in a porous carbon matrix and elemental iron either deposited thereon or substantially uniformly dispersed therein, wherein the concentration of active carbon in the catalyst is from about 20 to about 90 weight percent, based on the weight of the catalyst, wherein the concentration of elemental iron in the catalyst is from about 5 to about 50 weight percent, based on the weight of the catalyst, wherein the total concentration of the chromium component, the aluminum component, the manganese component or tungsten component or a combination thereof in the catalyst is from about 5 to about 40 weight percent, based on the weight of the catalyst and calculated as the elemental metal or metals, and wherein each of the chromium, aluminum, manganese and tungsten components that is present is in the form of the elemental metal, its oxide or a combination thereof.

* * * * *

UNITED STATES PATENT OFFICE
CERTIFICATE OF CORRECTION

Patent No. 4,513,096              Dated   April 23, 1985

Inventor(s) JOHN F. CONNOLLY - ARNOLD N. WENNERBERG - ROBERT F. WATERS

It is certified that error appears in the above-identified patent and that said Letters Patent are hereby corrected as shown below:

Col. Line 15   64-65   "13-1-5—6.8" (5 in bold face) should be
             -- 13-15—6.8 -- (and 5 in regular type)

Signed and Sealed this

Twentieth Day of August 1985

[SEAL]

Attest:

DONALD J. QUIGG

Attesting Officer    Acting Commissioner of Patents and Trademarks